United States Patent [19] [11] Patent Number: 4,980,154
Gordon [45] Date of Patent: Dec. 25, 1990

[54] TOOTH AND GUM DENTIFRICE COMPOSITION AND METHOD OF MAKING SAME

[76] Inventor: Norman Gordon, 114 Sussex Rd., New Rochelle, N.Y. 10804

[21] Appl. No.: 210,384

[22] Filed: Jun. 23, 1988

[51] Int. Cl.$^5$ .................. A61K 7/18; A61K 7/20; A61K 7/22; A61K 9/50
[52] U.S. Cl. .................. 424/53; 424/71; 424/52; 424/613; 514/588; 514/900; 514/902; 514/963
[58] Field of Search .............. 424/495, 253, 613, 616; 428/403, 401, 402.24; 514/588, 900, 902, 963

[56] References Cited

U.S. PATENT DOCUMENTS

| | | | |
|---|---|---|---|
| 1,018,240 | 2/1912 | Foregger | 424/53 |
| 2,430,450 | 11/1947 | Brown et al. | 514/588 |
| 2,436,673 | 2/1948 | Shelton | 424/613 |
| 2,542,898 | 2/1951 | Brown et al. | 514/588 |
| 3,574,824 | 4/1971 | Echeandia et al. | 424/50 |
| 3,957,964 | 5/1976 | Grimm | 424/10 |
| 4,132,771 | 1/1979 | Schreiber et al. | 424/52 |
| 4,162,165 | 7/1979 | Schwab | 424/403 |
| 4,202,878 | 5/1980 | Ritze | 424/7.7 |
| 4,293,426 | 10/1981 | Gago | 428/403 |
| 4,376,762 | 3/1983 | Hauschild et al. | 424/7.1 |
| 4,470,839 | 9/1984 | Gago | 428/403 |
| 4,522,805 | 6/1985 | Gordon | 424/53 |
| 4,582,701 | 4/1986 | Piechota | 424/49 |
| 4,603,045 | 7/1986 | Smigel | 424/52 |
| 4,608,277 | 8/1986 | Greiner et al. | 428/407 |
| 4,663,152 | 5/1987 | Barth et al. | 424/7.1 |
| 4,687,663 | 8/1987 | Schaeffer | 424/52 |
| 4,776,500 | 10/1988 | Ford | 424/53 |
| 4,837,008 | 6/1989 | Rudy et al. | 424/53 |
| 4,867,988 | 9/1989 | Chernack | 424/616 |
| 4,897,258 | 1/1990 | Rudy et al. | 424/53 |

FOREIGN PATENT DOCUMENTS

| | | | |
|---|---|---|---|
| 559142 | 6/1958 | Canada | 424/613 |
| 2513119 | 3/1983 | France | 424/613 |

OTHER PUBLICATIONS

King, O. G. 8/21/51, vol. 649, p. 691.

Primary Examiner—Shep K. Rose
Attorney, Agent, or Firm—Arthur T. Fattibene

[57] ABSTRACT

A tooth and gum paste in the form of a staple composition for controlling peridontal disease, reduction of plaque and oral oders in which one or more of the ingredients is microencapsulated within the composition.

8 Claims, 1 Drawing Sheet

TOOTH AND GUM DENTIFRICE COMPOSITION AND METHOD OF MAKING SAME

FIELD OF INVENTION

This invention relates to a tooth and gum dentifrice composition, and more specifically to a tooth and gum dentifrice composition in the form of a stable paste for controlling and/or minimizing incipient peridontal disease and for aiding in the reduction of plaque in which one or more of the ingredients is microencapsulated within the composition.

PRIOR ART

This invention relates to an improvement in a tooth and gum dentifrice of a type disclosed in my prior U.S. Pat. No. 4,522,805 granted Jun. 11, 1985 entitled Tooth and Gum Dentifrice. While the tooth and gum dentifrice disclosed in my prior patent proved effective for its intended purpose, experience has shown that further improvements thereto were desirable, particularly with respect to matters relating to extending the shelf life of the product and/or for improving the handling and storage of the dentifrice. It has been noted that when the patented dentifrice disclosed in U.S. Pat. No. 4,522,805 was stored in an environment where an excessive rise in temperature may occur, there was a tendency for the ingredients to react or decompose, which would minimize the efficacy of the dentifrice. In a normal or cool environment, the stability of the dentifrice could be maintained.

OBJECTS

An object of this invention is to provide a tooth and gum dentifrice for controlling incipient peridontal disease and/or aiding the reduction of plaque that is formulated so as to withstand any tendency to react or decompose when subjected to an enviroment of abnormally high temperatures, e.g. temperatures in excess of 100° F. during storage and/or handling.

Another object of this invention is to provide a tooth and gum dentifrice in which certain of the ingredients thereof are microencapsulated to prevent decomposition and/or inter-reaction until used.

Another object is to provide a tooth and gum dentifrice in which one or more of the ingredients are microencapsulated in multi-colored pellets suspended in the dentifrice.

Another object is to provide a tooth and gum paste in the form of an effective and stable paste composition.

Another object is to provide a tooth and gum dentifrice to effect the synergism of actions in a singular composition that can be readily applied to the teeth and gum by conventional brushing.

Another object is to provide a tooth and gum dentifrice which is formulated to synergistically effect the removal of dental plaque and/or to reduce the formation of tartar and surface stains on teeth.

Another object is to provide for a tooth and gum dentifrice that is capable of reducing the bacterial count by its antiseptic action.

Another object is to provide a tooth and gum dentifrice capable of oxygenating the gum tissues.

Another object is to provide a tooth and gum dentifrice for aiding in the prevention of peridontal disease by its chemical and mechanical actions.

Another object is to provide a tooth and gum dentifrice for reducing oral odors by inhibiting the odor forming bacteria.

Another object is to provide a tooth and gum dentifrice which aids in the reduction of dental caries.

Another object is to provide a tooth and gum dentifrice which aids in combining chemically with the enamel structure of a tooth so as to render the tooth more resistant to dental caries by enhancing the hardness of the tooth enamel so as to render the tooth enamel less likely to demineralize by acid produced from any adhering bacteria.

SUMMARY OF THE INVENTION

The foregoing objects and other features and advantages are attained by a tooth and gum dentifrice which is formulated as a stable paste comprising approximately 15to 25% by weight of sodium bicarbonate, approximately 10 to 20% by weight of calcium carbonate either in its normal or in a microencapsulated form; approximately 3.5 to 11% by weight of microencapsulated calcium peroxide; approximately 1.25 to 3% by weight of sodium fluoride in either its natural or microencapsulated form; approximately 0.5 to 1.5% by weight of urea; and the remainder or approximately 40% to 71% by weight of a paste that includes a detergent, humectant (sorbitol), a thickening agent or binder and a flavoring agent.

FEATURES

A feature of this invention resides in the provision of microencapsulating the calcium peroxide ingredient of the formulation and dispensing the same throughout the mixture as micro pellets which may be multi-colored.

Another feature resides in the provision whereby the calcium carbonate and sodium fluoride ingredients can be optionally microencapsulated and likewise disbursed throughout the mixture.

Another feature resides in the provision wherein the dentifrice effects a clinical production of oxygen and a release of ammonia to aid in the reduction of harmful oral bacteria.

Other features and advantages will become more readily apparent when considered in view of the drawing and specification in which.

DETAIL DESCRIPTION

This invention is directed to a tooth and gum dentifrice in the form of a paste which is composed of a combination of various selected ingredients to form a stable composition which synergistically effects a chemical and mechanical action to effect the removal and/or minimizes any build up of plaque on the teeth and to reduce the bacterial level. The resultant effect is to aid in the control and removal of incipient peridontal disease as well as to aid in the reduction of dental caries. Essentially, the tooth and gum dentifrice comprises a formulation containing sodium bicarbonate, urea, calcium carbonate, calcium peroxide/microencapsulated dispensed in a paste carrier which includes a detergent which may be natural or synthetic, a humectant (sorbitol), a thickening agent or binder and a flavoring agent. The formulation may also contain fluoride, e. g. a fluoride that has been shown to be effective in aiding the tooth enamel to become hardened and resistant to caries. The preferred calcium peroxide is one in a water-free base.

Figure 1:
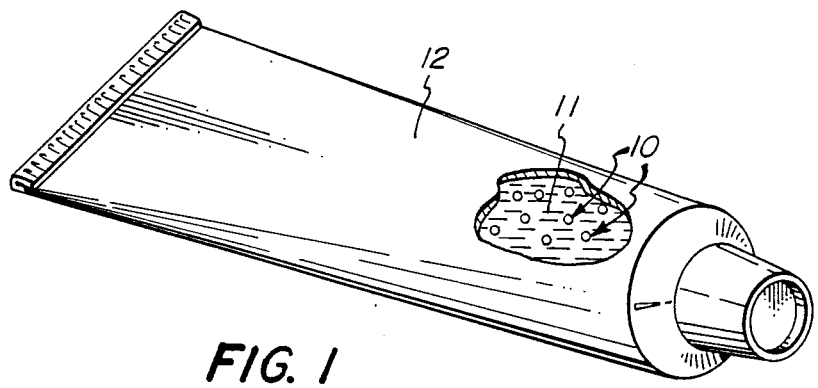
FIG. 1 is a perspective view of a package containing the tooth and gum dentifrice embodying the invention.
Figure 2:
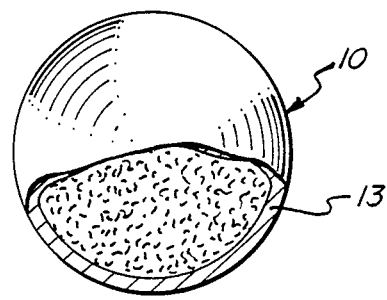
FIG. 2 illustrates a microencapsulated component of the present invention.

The tooth and gum formulation comprises from 15 to 25% by weight of sodium bicarbonate, from 10 to 20% by weight of calcium carbonate, from 3.5 to 11% of calcium peroxide, which, according to this invention, is microencapsulated in micro-pellet 10 as shown in FIG. 2, and dispersed throughout the paste composition 11 as noted in FIG. 1. The formulation also includes from 1.25 to 3% by weight of sodium fluoride and from 0.5 to 1.5% by weight of urea. The foregoing described ingredients are mixed into a paste carrier comprising approximately from 41% to 71% by weight that includes a detergent, humectant (sorbitol), a thickening agent or binder and a flavoring agent. The dentifrice is preferably compounded by mixing the ingredients of the base paste or carrier with the appropriate portion of sodium bicarbonate, followed by mixing the specified quantities of calcium carbonate and calcium peroxide. Upon completion of the homogenized mix, the formulation is then placed in a light resistant and moisture-proof container or tube 12 as shown in FIG. 1.

Optionally, the calcium carbonate and sodium fluoride ingredients may also be microencapsulated as micro pellet and dispersed throughout the carrier or paste 11. The coating 13 in which the calcium peroxide is encapsulated comprises an ethyl cellulose with epolene wax known as C-10 as sold by Eastman Kodak. The calcium carbonate and sodium fluoride ingredients may be similarly coated for microencapsulation. If more than one ingredient is microencapsulated, they can be optionally encapsulated in coatings of different colors whereby the respective ingredients can be separately identified.

In the formulation, as herein set forth, the calcium peroxide micro-pellets adhere to the tissues and thereby remain in place for a relatively long period of time while releasing nascent oxygen to aid in debriding tissues and to inhibit any odor-forming bacteria. It also effects a foaming action which mechanically tends to raise the plaque and bacteria from incipient peridontal lesions and prevents them from releasing their destructive enzymes in the gingival pockets.

As the urea reaches the oral cavity, it dissociates into ammonia ($NH_3$). The calcium peroxide, in the paste, when combined in an aqueous environment produces hydrogen peroxide ($H_2O_2$), which in the presence of peroxidase and catalase, cause the release of free oxygen. Free oxygen and ammonia have a cidal effect on bacteria to produce an anti-caries and anti-plaque effect. In the bacterial plaque, the urea is turned into $NH_3$ and carbonic acid by the enzyme urease. This raises the acidified plaque to a more neutral pH and reduces the rate of tooth demineralization to render the tooth more resistant to caries by fermented carbohydrates. Thus, in the described formulation, urea has an anti-caries and anti-plaque effect.

The calcium carbonate ($CaCO_3$) portion of the formulation is used as a mild abrasive and polishing agent. It, too, performs a mechanical action on the teeth to also aid in the removal of plaque and bacteria therefrom, as well as any food particles and stains from the tooth structure.

The sodium bicarbonate ($NaHCO_3$) portion of the formulation also has a mildly abrasive action on the teeth to effect the removal of dental plaque, bacteria, food particles and stain from the tooth surfaces. It also aids in neutralizing odors.

Also included in the formulation is a fluoride for combining chemically into the enamel structure of the teeth to form a flour-apatite so as to cause the enamel to become harder, and thereby render the teeth less likely to be demineralized by the acids formed by adhering bacteria and their action on sugar substances. Fluorides have also been shown to retard the rapidity of pre-existing dental caries.

EXAMPLE 1

The general formulation of the tooth and gum dentifrice is comprised as follows:
Sodium bicarbonate ranging from 15-25% by weight. The sodium bicarbonate may include a #325 grit.
Calcium carbonate ranging from 10-20% by weight.
Calcium peroxide (microencapsulated) from 3.5 to 11% by weight.
Urea ranging from 0.5 to 1.5% by weight.
Sodium fluoride from 1.25-3.0% by weight.
A paste carrier comprises a mixture of a detergent, a humectant (sorbitol), and a thickening agent or binder. Also, the paste may be flavored by a suitable flavoring agent. A preferred paste or carrier may include: 4-10% by weight of sorbitol, 1.5%-3.85% by weight of sodium lauryl sulfate. Remainder by weight comprising miscellaneous binders which may include flavor, sweeteners and a preservative.

The thickening agent or binder prevents the separation of the liquid and solid ingredients. The thickening agent or binder comprised of gum tragacant and gum karaya (natural) seaweed colloid-sodium alginate and synthetic cellulose, i.e., Na carboxymethylcellulose or methylcellulose. A foaming agent such as sodium lauryl sulfate and sodium-N-laurylsacrosinate. A sweetner such as saccharin, asparatine and/or a suitable flavoring ingredient such as mint or the like may be included in the paste or carrier portion.

The tooth and gum dentifrice functions as a toothpaste, antiplaque, antitartar, oxygenating agent, stain remover, antiseptic and odor inhibitor.

| mg/gram | Ingredient | Grade | Function |
| --- | --- | --- | --- |
| | DRY MIX | | |
| 208.3 | Sodium bicarbonate | USP | cl. agent |
| 150.0 | Calcium carbonate | USP xtra | polish |
| 56.6 | Calcium peroxide (microencapsulated) | Food grade | antisept |
| | WET MIX | | |
| 416.0 | Propylene glycol | USP | vehicle |
| 20.0 | Methylcellulose | NF powder | vehicle |
| 29.3 | Sodium lauryl sulfate | NF powder | deterg |
| 2.0 | Sodium fluoride | USP | active |
| 75.0 | Sorbitol | NF powder | vehicle |
| 3.0 | Sodium saccharin | USP | flavor |
| 29.3 | Fumed silica | USP | polish |
| 1.0 | Urea | USP | antisept |
| 5.0 | Spearment (or any other appropriate flavoring) | FDA/GRAS | flavor |
| 3.0 | Magnasweet 100 | FDA/GRAS | flavor |

It is preferred that the solids be fine milled so as to pass through a #50 sieve. All equipment should be of a stainless steel or other non-reactive material; and any moisture additions which the manufacturing process may contribute are to be avoided.

A preferred manufacturing procedure is to first heat the propylene glycol in a suitable vessel and maintain at a temperature of 55°-65° C. Add thereto all the materials listed in the liquid (wet) phase in the order noted following Example 3 with a slow mixing; allowing sufficient time for each material to dissolve or disperse; approximately 8 to 10 minutes, before the next material is added. Upon the mixing herein set forth, the heat is discontinued. The last component of the wet phase is slowly mixed for a period of 2-5 minutes. The sweetener and flavoring agent is then added. The mix is then brought to room temperature, 18°-23° C. while mixing. The dry ingredients, listed above, are then added in the order listed, allowing each sufficient time to be fully wetted and uniformly blended; about 10 to 12 minutes. The resulting mix may be mulled, if deemed necessary, by any suitable means, and thereafter filled into plastic lined or other non-reactive containers or tubes; which are light resistant and moisture proof.

The tooth and gum paste so formulated, is preferably used immediately after meals, or as soon thereafter as feasible. The formulated paste when used in conjunction with dental floss interproximally enables the preparation to be further dispensed into the incipient peridontal pockets to enhance the formulation in the reduction of food, plaque and bacterial action.

EXAMPLE 2

A specific tooth and gum dentifrice is made as follows:

| | |
|---|---|
| Sodium bicarbonate | 15% by weight |
| Calcium carbonate | 10% by weight |
| Calcium peroxide | 3.5% by weight (microencapsulated) |
| Urea | 0.5% by weight |
| Paste carrier | 71.0% by weight | whereby the paste is formulated of the ingredients set forth in Example 1.

EXAMPLE 3

Another specific formulation of the tooth and gum dentifrice comprises:

| | |
|---|---|
| Sodium bicarbonate | 25% by weight |
| Calcium carbonate | 20% by weight |
| Calcium peroxide (microencapsulated) | 11% by weight |
| Urea | 1.5% by weight |
| Paste carrier | 42.5% by weight | wherein the paste is formulated of the ingredients defined in Example 1.

| | |
|---|---|
| Sodium bicarbonate | 25% by weight |
| Calcium carbonate | 20% by weight |
| Calcium peroxide (microencapsulated) | 11% by weight |
| Urea | 1.5% by weight |
| Paste carrier | 42.5% by weight |

The combination of the foregoing noted ingredients form an effective and stable paste composition which givesit the ability to aid in the prevention of gum (peridontal) disease and aid in the reduction of dental caries, as well as to inhibit the more rapid spread of the decay process. The foregoing formulation further effects a stable composition to effect a synergism of actions in a singular preparation which can be readily applied to the teeth and gums by conventional brushing.

The above formulation represents a heat stable product. Its appearance can be multi-colored pellets suspended in a paste carrier. When the formula comes in contact with the saliva, it immediately becomes active in chemically and mechanically removing tooth stain, plaque, tartar and inhibiting bacterial flora that contribute to the incidence of peridontal disease and dental caries and oral odors.

While the present invention has been described with respect to a particular embodiment, it will be understood that variations and modifications can be made without departing from the spirit or scope of the invention.

What is claimed is:

1. A tooth and gum dentifrice composition in the form of a stable paste for controlling and minimizing incipient periodontal disease and for aiding in the reduction of plaque comprising approximately 15% to 25% by weight of sodium bicarbonate, approximately 10% to 20% by weight of calcium carbonate, approximately 3.5% to 11% by weight of calcium peroxide in microencapsulated form, approximately 0.5% to 1.5% by weight of urea, and approximately 42.5% to 71% by weight of a carrier that is free of water, said sodium bicarbonate, calcium carbonate, encapsulated calcium peroxide, and urea being mixed in said carrier, whereby said urea disassociates into ammonia and calcium peroxide in the presence of the aqueous environment of the oral cavity to produce hydrogen peroxide which in the presence of peroxidase and catalase, causes the release of free oxygen whereby said free oxygen and ammonia produces an enhanced cidal effect on bacteria to produce an anti-caries and anti-plaque effect.

2. A tooth and gum dentifrice composition as defined in claim 1 wherein said carrier is a paste comprising a synthetic detergent, humectant and a binder.

3. A tooth and gum dentifrice composition as defined in claim 2 and including a flavoring agent.

4. A tooth and gum dentifrice composition in the form of a stable paste for aiding in the control and removal of peridontal lesions and for the removal of dental plaque and minimizing dental caries comprising
    approximately 15% by weight of sodium bicarbonate
    approximately 10% by weight of calcium carbonate
    approximately 3.5% by weight of calcium peroxide (microencapsulated)
    approximately 1.25% by weight of sodium fluoride
    approximately 0.5% by weight of urea
    the remainder of a paste of a mixture of synthetic detergent containing a humectant and a thickening agent
whereby said urea disassociates into ammonia and calcium peroxide in the presence of the aqueous environment of the oral cavity to produce hydrogen peroxide which in the presence of peroxidase and ctalase, causes the release of free oxygen whereby said free oxygen and ammonia produces an enhanced cidal effect on bacteria to produce an anti-caries and anti-plaque effect.

5. A tooth and gum dentifrice as defined in claim 4 wherein said remainder paste includes a flavoring agent.

6. A tooth and gum dentifrice composition in the form of a stable paste for controlling and minimizing incipient periodontal disease and for aiding in the reduction of plaque comprising:
    a water soluble non aqueous paste carrier including a natural or synthetic detergent, a humectant, a thickening agent and a flavoring agent and having dispersed therein sodium bicarbonate, calcium carbonate, calcium peroxide, and urea, and said calcium peroxide being encapsulated in a water soluble coating, and said composition being anhydrous, and the relative proportions of said calcium peroxide and urea being sufficient such that upon reaching the oral cavity, the urea disassociates into ammonia and the calcium peroxide in the presence of the aqueous environment of the oral cavity produces hydrogen peroxide which, in the presence of peroxidase and catalase, causes the release of free oxygen whereby said free oxygen and ammonia have an enhanced cidal effect on bacteria to produce an anti-caries and anti-plaque effect.

7. The composition in accordance with claim 6, wherein said paste carrier includes a fluoride effective in hardening the tooth enamel.

8. A tooth and gum dentifrice composition in the form of a stable paste for aiding in the control and removal of peridontal lesions and for the removal of dental plaque, tartar and stain, and for minimizing dental caries comprising:

approximately 25% by weight of sodium bicarbonate
approximately 20% by weight of calcium carbonate
approximately 11% by weight of microencapsulated calcium peroxide,
approximately 3% by weight of sodium peroxide
approximately 1.5% by weight of urea
the remainder of a paste of a mixture of synthetic detergent, a humectant (sorbitol), a binder and a flavoring agent, whereby said composition is heat stable and upon contact with the saliva, becomes chemically and mechanically active in removing tooth stain, plaque, tartar and inhibiting bacterial flora that contribute to the incidence of peridontal disease, dental caries and oral odors, as said urea disassociates into ammonia and the calcium peroxide in the presence of the aqueous environment of the oral cavity to produce hydrogen peroxice which in the presence of peroxidase and catalase, causes the release of free oxygen whereby said free oxygen and ammonia produces an enhanced cidal effect on bacteria to produce an anti-caries and anti-plaque effect.

* * * * *